United States Patent
Kustra et al.

(10) Patent No.: US 11,717,268 B2
(45) Date of Patent: Aug. 8, 2023

(54) ULTRASOUND IMAGING SYSTEM AND METHOD FOR COMPOUNDING 3D IMAGES VIA STITCHING BASED ON POINT DISTANCES

(71) Applicant: KONINKLIJKE PHILIPS N.V., Eindhoven (NL)

(72) Inventors: Jacek Lukasz Kustra, Eindhoven (NL); Edmond van Dijk, Eindhoven (NL); Guillaume Leopold Theodorus Frederik Hautvast, Veldhoven (NL); Dave Senden, Eindhoven (NL); Dirk Binnekamp, Weerselo (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 422 days.

(21) Appl. No.: 16/349,447

(22) PCT Filed: Nov. 24, 2017

(86) PCT No.: PCT/EP2017/080285
§ 371 (c)(1),
(2) Date: May 13, 2019

(87) PCT Pub. No.: WO2018/099810
PCT Pub. Date: Jun. 7, 2018

(65) Prior Publication Data
US 2019/0336110 A1 Nov. 7, 2019

(30) Foreign Application Priority Data
Nov. 29, 2016 (EP) .................................... 16201057

(51) Int. Cl.
*A61B 8/08* (2006.01)
*A61B 8/00* (2006.01)
*G01S 15/89* (2006.01)

(52) U.S. Cl.
CPC ............ *A61B 8/5253* (2013.01); *A61B 8/463* (2013.01); *A61B 8/5207* (2013.01); *A61B 8/4254* (2013.01);
(Continued)

(58) Field of Classification Search
CPC ....... A61B 8/4254; A61B 8/463; A61B 8/483; A61B 8/5207; A61B 8/5253; G01S 15/8993; G01S 15/8995
See application file for complete search history.

(56) References Cited

U.S. PATENT DOCUMENTS

| | | |
|---|---|---|
| 5,997,479 A | 12/1999 | Savord et al. |
| 6,013,032 A | 1/2000 | Savord |

(Continued)

OTHER PUBLICATIONS

Flach et al., "PURE: Panoramic Ultrasound Reconstruction by Seamless Stitching of Volumes", Simulation and Synthesis in Medical Imaging. SASHIMI 2016. Lecture Notes in Computer Science, vol. 9968., (Sep. 2016), p. 75-84 (Year: 2016).*

(Continued)

*Primary Examiner* — Serkan Akar

(57) ABSTRACT

The present invention relates to an ultrasound imaging system (100) for producing spatially compounded 3D ultrasound image data, comprising: —an ultrasound acquisition unit (16) for acquiring a plurality of 3D ultrasound image data having different but at least partially overlapping field of views, —a tracking unit (62) adapted to determine a relative spatial position of each of the plurality of 3D ultrasound image data with respect to each other, and —a stitching unit (64) adapted to compound the plurality of 3D ultrasound image data by stitching them to each other in order to generate compounded 3D ultrasound image data, wherein the stitching unit (64) is adapted to calculate a stitching order of the plurality of 3D ultrasound image data based on the determined relative spatial position of the 3D (Continued)

ultrasound image data by minimizing an overlapping area of the different field of views of the plurality of 3D ultrasound image data, and wherein stitching unit (64) is adapted to stitch the plurality of 3D ultrasound image data according to said stitching order.

11 Claims, 4 Drawing Sheets

(52) U.S. Cl.
CPC .......... *A61B 8/483* (2013.01); *G01S 15/8993* (2013.01); *G01S 15/8995* (2013.01)

(56) References Cited

U.S. PATENT DOCUMENTS

| | | | |
|---|---|---|---|
| 6,224,552 B1 | 5/2001 | Jago et al. | |
| 6,283,919 B1 | 9/2001 | Roundhill et al. | |
| 6,443,896 B1 | 9/2002 | Detmer | |
| 6,458,083 B1 | 10/2002 | Jago et al. | |
| 6,540,681 B1 | 4/2003 | Cheng et al. | |
| 6,623,432 B2 | 9/2003 | Powers et al. | |
| 2001/0014773 A1 | 8/2001 | Jago | |
| 2003/0086492 A1* | 5/2003 | Hori | H04N 19/20 375/240.08 |
| 2004/0127794 A1* | 7/2004 | Murashita | G01S 15/8993 600/442 |
| 2005/0033173 A1* | 2/2005 | Von Behren | A61B 8/00 600/443 |
| 2006/0235301 A1 | 10/2006 | Chalana et al. | |
| 2007/0255137 A1 | 11/2007 | Sui et al. | |
| 2010/0130855 A1 | 5/2010 | Lundberg et al. | |
| 2010/0179428 A1* | 7/2010 | Pedersen | A61B 8/4254 600/443 |
| 2011/0125022 A1 | 5/2011 | Lazebnik | |
| 2011/0306025 A1* | 12/2011 | Sheehan | A61B 8/4245 434/267 |
| 2013/0012819 A1 | 1/2013 | Haugen et al. | |
| 2014/0267267 A1* | 9/2014 | Piper | G09G 5/377 345/424 |
| 2014/0358003 A1 | 12/2014 | Ueda et al. | |
| 2015/0133784 A1 | 5/2015 | Kapoor et al. | |
| 2015/0196278 A1* | 7/2015 | Noguchi | A61B 8/5207 600/447 |
| 2016/0088287 A1* | 3/2016 | Sadi | H04N 13/194 348/43 |
| 2016/0100821 A1* | 4/2016 | Eggers | A61B 8/483 600/424 |

OTHER PUBLICATIONS

Wang, "Simulation, Stitching, and Interaction Techniques for Large-Scale Ultrasound Datasets", University of California (Dissertation), (2016), p. 1-123. (Year: 2016).*

Drum, W.R., et al., "Non-rigid image registration: theory and practice", the British Journal of Radiology 2004, pp. 140-153.

Herraez J et al., "Optimal modelling of buildings through simultaneous automatic simplifications of point clouds obtained with a laser scanner", Measurement, Institute of Measurement and Control. London, GB, vol. 93, Jun. 21, 2016, pp. 243-251.

* cited by examiner

ULTRASOUND IMAGING SYSTEM AND METHOD FOR COMPOUNDING 3D IMAGES VIA STITCHING BASED ON POINT DISTANCES

CROSS-REFERENCE TO PRIOR APPLICATIONS

This application is the U.S. National Phase application under 35 U.S.C. § 371 of International Application Serial No. PCT/EP2017/080285, filed on Nov. 24, 2017, which claims the benefit of European Patent Application No. 16201057.3, filed on Nov. 29, 2016. This application is hereby incorporated by reference herein.

FIELD OF THE INVENTION

The present invention relates to an ultrasound imaging system for producing spatially compounded 3D ultrasound image data from a plurality of consecutive 3D ultrasound image data having different but at least partially overlapping field of views.

The present invention furthermore relates to a corresponding ultrasound imaging method as well as to a computer program for carrying out said method.

BACKGROUND OF THE INVENTION

Ultrasound imaging is commonly used in several diagnostic, therapeutic and interventional contexts, such as biopsy or brachytherapy. The most common ultrasound probes provide a close to real-time stream of two-dimensional images, which are interactively visualized by the physician. However, given the three-dimensional properties of the human anatomy, a third dimension can be achieved by sweeping the probes and acquiring simultaneously the probe imaging data and its spatial position, followed by an interpolation of the values in places of the volume where imaging data is missing. In this approach, each voxel in the volume is interpolated to the acquired imaging data in its surroundings. This is a technique used in several products such as the Philips UroNav Biopsy solution.

Innovations in ultrasound probes, such as the Philips X7-2T matrix probe, allow for a close to real-time acquisition of 3D volumes. This allows the physician acquiring in one go a full volume, revealing the target anatomy, which can be used for diagnostics, planning or therapy purposes.

Although the matrix probe technology allows the acquisition of a full volume in one go, it has inherit limitations in the volume visible from the probe. In other words, each ultrasound probe has a limited field of view. This limits the applicability of matrix probes for applications requiring a full visibility of the target organ. For this purpose, several volumes need to be acquired with knowledge of their relative positioning. However, contrary to a two-dimensional image acquisition, the continuous (real-time) acquisition of 3D volumes leads to several overlapping volumes.

Trivial approaches, such as the selection of volumes by their age, i.e. the time and date of the image acquisition, causes issues when reconstructing the final volume, since the continuous acquisition leads to the presence of a large number of "stitching" points.

Known compounding techniques, such as the one proposed in U.S. Pat. No. 6,224,552 B1 allow combining several volumes into one large compounded volume. In this technique, the visibility of the seams/stitches occurring at the edges of the compounded image volumes are tried to be reduced by means of a special weighting technique. However, this does not minimize the number of seams/stitches which would be more favorable than reducing the visibility of the seams/stitches as proposed in U.S. Pat. No. 6,224,552 B1. Similar techniques as the one proposed in U.S. Pat. No. 6,224,552 B1 are known from US 2014/0267267 A1 and from US 2015/0133784 A1. However, also these techniques fail to minimize the number of seams/stitches.

US 2010/0179428 A1 discloses a virtual interactive ultrasound training system for training medical personnel in the practical skills of performing ultrasound scans, including recognizing specific anatomies and pathologies.

On the other hand, US 2016/0100821 A1 relates to hand-held imaging devices with position and/or orientation sensors for complete examination of tissue.

Since the optimal image intensity distribution is optimal for each individual volume, it is desired that the number of stitching areas in the reconstructed compounded volume is minimized.

SUMMARY OF THE INVENTION

It is therefore an object of the present invention to provide an ultrasound imaging system and method for producing spatially compounded 3D ultrasound image data, wherein the number of stitching areas in the reconstructed compounded 3D ultrasound image data are reduced as much as possible.

In a first aspect of the present invention, an ultrasound imaging system for producing spatially compounded 3D ultrasound image data is presented which comprises:
  an ultrasound acquisition unit for acquiring a plurality of 3D ultrasound image data having different but at least partially overlapping field of views,
  a tracking unit adapted to determine a relative spatial position of each of the plurality of 3D ultrasound image data with respect to each other, and
  a stitching unit adapted to compound the plurality of 3D ultrasound image data by stitching them to each other in order to generate compounded 3D ultrasound image data, wherein the stitching unit is adapted to calculate a stitching order of the plurality of 3D ultrasound image data based on the determined relative spatial position of the 3D ultrasound image data by minimizing an overlapping area of the different field of views of the plurality of 3D ultrasound image data, and wherein stitching unit is adapted to stitch the plurality of 3D ultrasound image data according to said stitching order.

In a second aspect of the present invention, an ultrasound imaging method for producing spatially compounded 3D ultrasound image data is presented, comprising the steps of:
  acquiring a plurality of 3D ultrasound image data having different but at least partially overlapping field of views,
  determining a relative spatial position of each of the plurality of 3D ultrasound image data with respect to each other, and
  calculating a stitching order of the plurality of 3D ultrasound image data based on the determined relative spatial position of the 3D ultrasound image data by minimizing an overlapping area of the different field of views of the plurality of 3D ultrasound image data, and
  compounding the plurality of 3D ultrasound image data by stitching them according to said stitching order.

In a further aspect of the present invention, a computer program is presented which comprises program code means for causing a computer to carry out the steps of the above-mentioned method when said computer program is carried out on a computer.

Preferred embodiments of the invention are defined in the dependent claims. It shall be understood that the claimed method and the claimed computer program have similar and/or identical preferred embodiments as the claimed system and as defined in the dependent claims.

The present invention proposes a novel approach for quickly computing an optimal selection of the 3D ultrasound data, prior to stitching them into the finally compounded 3D ultrasound image data. In contrast to the known compounding method mentioned in the introductory portion of this patent application, the present invention proposes calculating a stitching order of the plurality of 3D ultrasound image data by means of which the overlapping area of the different field of views of the plurality of stitched 3D ultrasound image data is minimized. The plurality of acquired 3D ultrasound image data are not simply stitched one after the other according to their acquisition time and date, e.g. beginning with the oldest one and ending up with the youngest data set. Instead, the plurality of 3D ultrasound image data are according to the present invention first ordered based on the relative spatial position at which the different data sets have been acquired. This relative spatial position of each of the 3D ultrasound image data with respect to each other is measured by means of a tracking unit.

Using this relative spatial position for ordering the 3D ultrasound image data prior to stitching them reduces the amount of stitches in the finally compounded 3D ultrasound image data and therefore increases the image quality of the finally compounded 3D ultrasound image.

According to a preferred embodiment, the stitching unit is adapted to calculate said stitching order by determining distances between spatial positions of center points of each of the plurality of 3D ultrasound image data, and ordering the plurality of 3D ultrasound image data according to said determined distances.

This minimizes the overlapping area between consecutive 3D ultrasound data. The compounded volumes are in other words ranked based on the overlapping area of the volumes in correlation to the distance between the volumes. This ranking results in sorting the volumes in correlation to or according to these distances. The aforementioned correlation is inverse. The further the distance of the "next" volume, the higher the "next" volume is "ranked". The named center points of each of the plurality of 3D ultrasound image data are preferably the center-of-mass points of each of the 3D ultrasound image data volumes or the ultrasound cone. That is, the center points of each of the plurality of 3D ultrasound image data are preferably the center-of-mass points of respective 3D ultrasound image data volumes. In ultrasound, the generated volume is larger than the actual data on it, which has a form of a cone (in 3D). Therefore, the actual ultrasound data is in a subset of the volume.

As already mentioned, the overlapping area of the consecutively acquired overlapping 3D ultrasound volumes are correlated to the distance between said volumes. This means, the further away the volumes are from each other, the smaller the overlapping area is, until a given threshold, over which the overlapping area is zero.

According to a further embodiment, the stitching unit is adapted to begin the stitching with one of the plurality of 3D ultrasound image data that has been acquired comparatively the latest in time and stitching it to another one of the plurality of 3D ultrasound image data, the center point of which having the comparatively largest distance from the center point of 3D ultrasound image data that has been acquired comparatively the latest in time.

In other words, the algorithm starts with the latest acquired, i.e. the youngest 3D ultrasound image data set, then selects the farthest distance 3D ultrasound image data set, i.e. the 3D data set which has the smallest overlapping area with the youngest 3D ultrasound data set that is taken for the beginning. This principle of always choosing the next 3D ultrasound data set to be stitched having the farthest distance from the already stitched data sets, i.e. the smallest overlapping area with the already stitched data sets, is then continued. This means that in the next step a 3D ultrasound image data set is selected, the center point of which has the comparatively largest distance from the center points of the two already selected 3D ultrasound image data sets. The center point is preferably the geometrical center of the 3D image or the geometrical center of the imaging data (cone in ultrasound, which is a subset of the full volume).

In other words, according to this embodiment the stitching unit is adapted to continue stitching a further one of the plurality of 3D ultrasound image data with the already stitched 3D ultrasound image data, wherein the center point of the further one of the plurality of 3D ultrasound image data has the comparatively largest distance from the center points of each of the already stitched 3D ultrasound image data.

It shall be noted that this stitching order is always calculated before stitching the respective image data. However, the present invention is not limited to calculating the complete order before stitching all images. It may also be possible to select one image after the other according to the above-mentioned ordering principle and then directly stitching them to the compounded 3D ultrasound image data set. This would not change anything at the principle underlying the present invention and shall therefore also fall under the scope of the present invention as claimed in the appended claims. By selecting the voxel values in the final volume based on this ordering, it provides an approximation to the volume distribution which minimizes the presence of scenes/stitches in the final volume of the compounded 3D ultrasound image.

As already mentioned in the beginning, calculating the stitching order according to the above-mentioned principle requires tracking the spatial positions at which the plurality of 3D ultrasound image data with different but overlapping field of views have been taken. It is not necessarily required to determine the absolute positions at which each of the 3D ultrasound images are taken. At least, it is necessary to determine the relative positions, meaning the positions at which the 3D ultrasound image data are taken with respect to one another. However, also tracking the absolute positions may be even more advantageous.

Preferably, the distance from the center points of each of the already stitched 3D ultrasound image data to the center point of the further one of the plurality of 3D ultrasound image data is computed as the sum of the distances from the center point of each of the already stitched 3D ultrasound image data to the center point of the further one of the plurality of 3D ultrasound image data.

According to an embodiment, the tracking unit comprises an electromagnetic tracking unit for determining the position of the ultrasound acquisition unit.

Determining the position of the ultrasound acquisition unit over time enables determining the positions of each of the plurality of 3D ultrasound image data taken by the ultrasound acquisition unit. This provides, for each voxel in the acquired volume, a position in the three-dimensional space. The voxels of the different 3D ultrasound image data sets may thus easily be registered to one another.

According to an alternative embodiment, the tracking unit comprises an optical tracking unit (instead of or additionally to an electromagnetic tracking unit) for determining the position of the ultrasound acquisition unit. Such an optical tracking unit may include one or more cameras that track the position of the ultrasound acquisition unit from outside. It is this a further example of an external tracking, similar as the external tracking mentioned before by means of an electromagnetic tracking unit.

In a further embodiment, the tracking unit is adapted to compare the plurality of 3D ultrasound image data by means of an image analysis, and to perform an image registration thereupon. For example, a rigid image registration approach may be used. For example, a similar approach as the one disclosed in Crum, W. R., et al.: "Non-rigid image registration: theory and practice", the British Journal of Radiology 2004, pp. 140-153 may be used. The specific registration approach that is used is preferably selected depending on the tissue properties being scanned. In this scenario, the relative positions of the volume voxels are computed with respect to the previously acquired volume. To obtain a "global" positioning of all acquired volumes, the relative transformations of each volume in the sequence should be added. This approach may not require an external tracking of the image acquisition unit as proposed according to the afore-mentioned embodiments.

According to a further embodiment, the ultrasound imaging system comprises an image quality unit which is adapted to perform an image analysis of each newly acquired 3D ultrasound image data, and to calculate an image difference of the newly acquired 3D ultrasound image data and the compounded 3D ultrasound image data for determining an image quality factor for the newly acquired 3D ultrasound image data.

One key strength of ultrasound when compared to other imaging modalities, such as CT, is the fast (real-time) acquisition properties. For several applications, such as in ultrasound guided brachytherapy, an important purpose is to monitor the anatomy changes, and if they pass a certain threshold, the intervention should be adapted. However, by performing a large area ultrasound acquisition using a compounded 3D ultrasound image data as explained above, the real-time information is usually inherently lost. To overcome this limitation, the afore-mentioned embodiment provides an image quality factor that provides an indication of the amount of image changes over time. The image quality unit computes for each image acquisition, the image difference between the newly acquired image data and the full volume of the compounded image data. The matric used for compounding the image difference may provide an absolute value providing an indication of the amount of image changes.

According to a further embodiment, the ultrasound imaging system comprises a display and a display control unit, wherein the display control unit is adapted to control the display to display the determined image quality factor. Alternatively or additionally, the ultrasound imaging system according to the present invention may include an alarm unit which is adapted to generate an optical, audible and/or haptic alarm if the image quality factor is below a predetermined threshold value. This may give the user a feedback regarding the image quality factor and, if necessary, warm him/her in cases of a too large image difference requiring a new image acquisition.

Preferred embodiments of the invention are defined in the dependent claims. It shall be understood that the claimed method has similar and/or identical preferred embodiments as the claimed device and as defined in the dependent claims.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
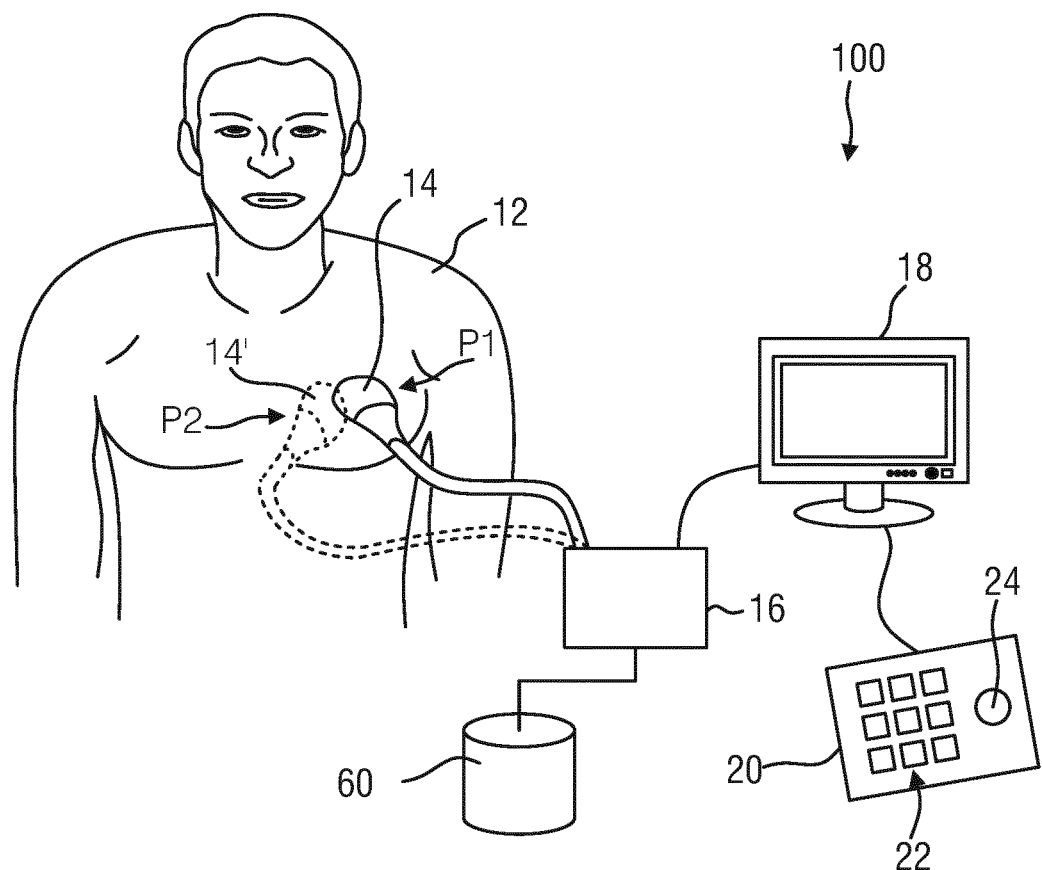
FIG. 1 shows a schematic representation of an ultrasound imaging system in use to scan a part of a patient's body.

FIG. 1 shows a schematic illustration of an ultrasound imaging system 100, in particular a medical three-dimensional (3D) ultrasound imaging system. The ultrasound imaging system 100 is applied to inspect a volume of an anatomical site, in particular an anatomical site of a patient 12 over time. The ultrasound system 100 comprises an ultrasound probe 14 having at least one transducer array having a multitude of transducer elements for transmitting and/or receiving ultrasound waves. In one example, each of the transducer elements can transmit ultrasound waves in form of at least one transmit impulse of a specific pulse duration, in particular a plurality of subsequent transmit pulses. The transducer elements are preferably arranged in a two-dimensional array, in particular for providing a multi-planar or three-dimensional image.

A particular example for a three-dimensional ultrasound system which may be the CX40 Compact Xtreme ultrasound system sold by the applicant, in particular together with a X6-1 or X7-2t TEE transducer of the applicant or another transducer using the xMatrix technology of the applicant. In general, matrix transducer systems as found on Philips iE33 systems or mechanical 3D/4D transducer technology as found, for example, on the Philips iU22 and HD15 systems may be applied in conjunction with the current invention.

A 3D ultrasound scan typically involves emitting ultrasound waves that illuminate a particular volume within a body, which may be designated as target volume or volumetric region. This can be achieved by emitting ultrasound waves at multiple different angles. A set of volume data is then obtained by receiving and processing reflected waves. The set of volume data is a representation of the target volume within the body over time. Since time is usually denoted as fourth dimension, such ultrasound system 100 delivering a 3D image sequence over time, is sometimes also referred to as a 4D ultrasound imaging system.

It shall be understood that the ultrasound probe 14 may either be used in a non-invasive manner (as shown in FIG.

1) or in an invasive manner as this is usually done in TEE (not explicitly shown). The ultrasound probe 14 may be hand-held by the user of the system, for example medical staff or a physician. The ultrasound probe 14 is applied to the body of the patient 12 so that an image of an anatomical site, in particular an anatomical object of the patient 12 is provided.

Further, the ultrasound system 100 may comprise an image reconstruction unit 16 that controls the provision of a 3D image sequence via the ultrasound system 100. As will be explained in further detail below, the image reconstruction unit 16 may control not only the acquisition of data via the transducer array of the ultrasound probe 14, but also signal and image processing that form the 3D image sequence out of the echoes of the ultrasound beams received by the transducer array of the ultrasound probe 14.

The ultrasound system 100 may further comprise a display 18 for displaying the 3D image sequence to the user. Still further, an input device 20 may be provided that may comprise keys or a keyboard 22 and further inputting devices, for example a trackball 24. The input device 20 may be connected to the display 18 or directly to the image reconstruction unit 16.

The ultrasound system 100 may further comprise a memory unit 60 for storing acquired ultrasound datasets. This memory unit 60 may either be provided separately to the remaining components such as the image reconstruction unit 16, or it may be provided in one an the same housing together with the image reconstruction unit 16.

Figure 2:
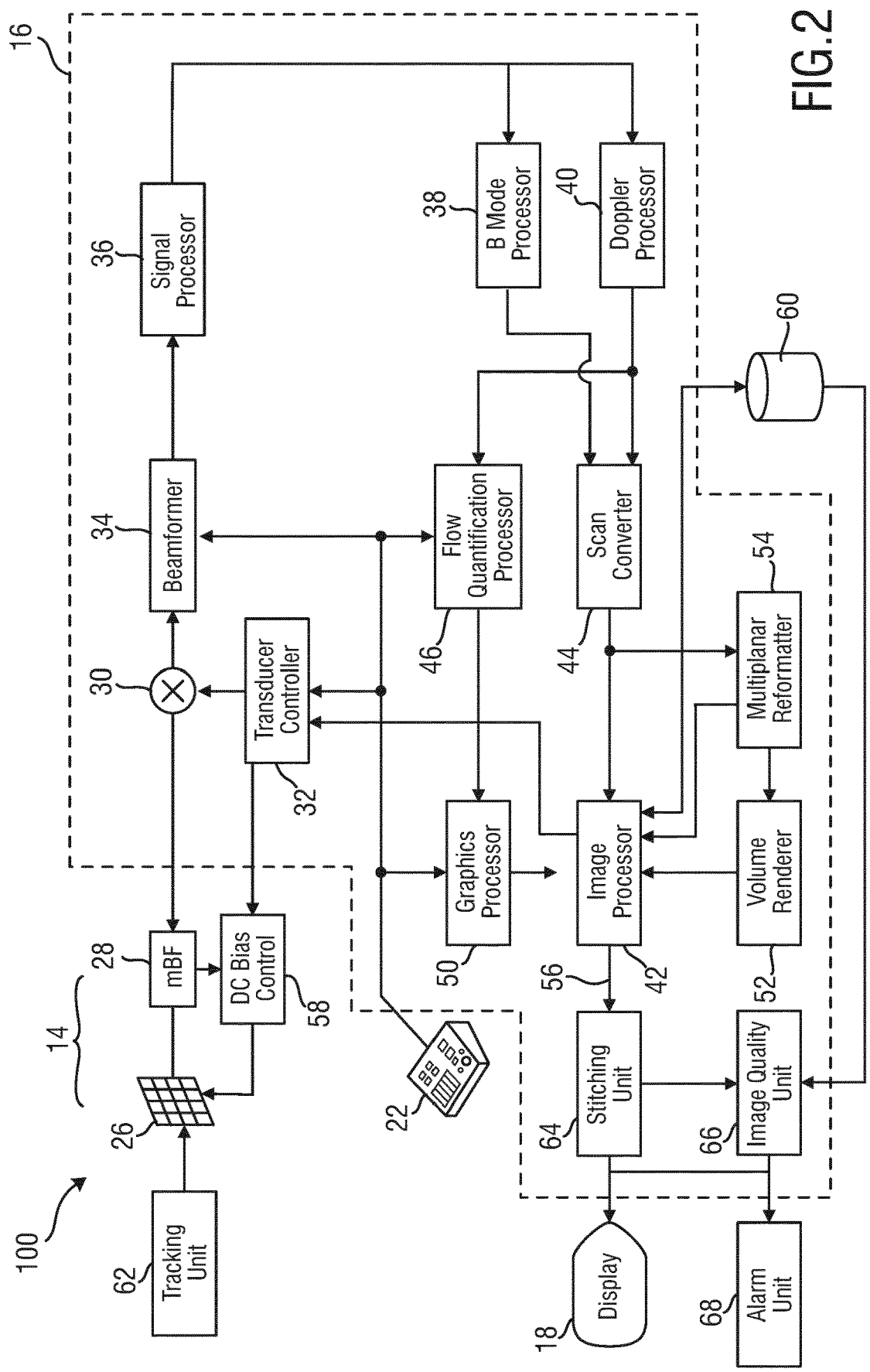
FIG. 2 shows a schematic block diagram of an embodiment of an ultrasound imaging system according to the present invention.

FIG. 2 illustrates a schematic block diagram of the ultrasound imaging system 100 illustrating several of its components. The ultrasound probe 14 may, for example, comprise a CMUT transducer array 26. The transducer array 26 may alternatively comprise piezoelectric transducer elements formed of materials such as PZT or PVDF. The transducer array 26 is a one- or a two-dimensional array of transducer elements capable of scanning in three dimensions for 3D imaging. The transducer array 26 is coupled to a microbeamformer 28 in the probe which controls transmission and reception of signals by the CMUT array cells or piezoelectric elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer 28 may be coupled by a probe cable to a transmit/receive (T/R) switch 30 which switches between transmission and reception and protects the main beamformer 34 from high energy transmit signals when a microbeamformer 28 is not used and the transducer array 26 is operated directly by the main beamformer 34. The transmission of ultrasonic beams from the transducer array 26 under control of the microbeamformer 28 is directed by a transducer controller 32 coupled to the microbeamformer 28 by the T/R switch 30 and the main system beamformer 34, which receives input from the user's operation of the user interface or control panel 22. One of the functions controlled by the transducer controller 32 is the direction in which beams are steered and focused. Beams may be steered straight ahead from (orthogonal to) the transducer array 26, or at different angles for a wider field of view. The transducer controller 32 can be coupled to control a DC bias control 58 for the CMUT array. The DC bias control 58 sets DC bias voltage(s) that are applied to the CMUT cells.

The partially beamformed signals produced by the microbeamformer 26 on receive are coupled to the main beamformer 34 where partially beamformed signals from individual patches of transducer elements are combined into a fully beamformed signal. For example, the main beamformer 34 may have 128 channels, each of which receives a partially beamformed signal from a patch of dozens or hundreds of CMUT transducer cells or piezoelectric elements. In this way the signals received by thousands of transducer elements of the transducer array 26 can contribute efficiently to a single beamformed signal.

The beamformed signals are coupled to a signal processor 36. The signal processor 36 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and/or microbubbles comprised in a contrast agent that has been pre-administered to the body of the patient 12. The signal processor 36 may also perform additional signal enhancement such as speckle reduction, signal compounding, and noise elimination. The bandpass filter in the signal processor 36 can be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals may be transferred to a B mode processor 38 and a Doppler processor 40. The B mode processor 38 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.).

The Doppler processor 40 may process temporally distinct signals from tissue movement and blood flow for the detection of the motion of substances such as the flow of blood cells in the image field. The Doppler processor 40 typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor 40 may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors 38, 40 may then be transferred to a scan converter 44 and a multiplanar reformatter 54. The scan converter 44 arranges the echo signals in the spatial relationship from which they were received in a desired image format. For instance, the scan converter 44 may arrange the echo signal into a two dimensional (2D) sector-shaped format, or a pyramidal three dimensional (3D) image. The scan converter 44 can overlay a B mode structural image with colors corresponding to motion at points in the image field with their Doppler-estimated velocities to produce a color Doppler image which depicts the motion of tissue and blood flow in the image field. The multiplanar reformatter 54 will convert echoes which are received from points in a common plane in a volumetric region of the body into an ultrasonic image of that plane, as described in U.S. Pat. No. 6,443,896 (Detmer). A volume renderer 52 converts the echo signals of a 3D data set into a projected 3D image sequence 56 over time as viewed from a given reference point as described in U.S. Pat. No. 6,530,885 (Entrekin et al.). The 3D image sequence 56 is transferred from the scan converter 44, multiplanar reformatter 54, and volume renderer 52 to an image processor 42 for further enhancement, buffering and temporary storage for display on the display 18. In addition to being used for imaging, the blood flow values produced by the Doppler processor 40 and tissue structure information produced by the B mode processor 38 may be transferred to a quantification processor 46. This quantification processor 46 may produce measures of different flow conditions such as the volume rate of blood flow as well as structural measurements such as the sizes of organs and gestational age. The quantification processor 46 may receive input from the user control panel 22, such as the point in the anatomy of an image where a measurement is to be made. Output data from the quantification processor 46 may be transferred to a graphics processor 50 for the reproduction of measurement graphics and values with the image on the display 18. The graphics processor 50 can also generate graphic overlays for display with the ultrasound images. These graphic overlays can contain standard identifying information such as patient name, date and time of the image, imaging parameters, and the like. For these purposes the graphics processor 50 may receive input from the user interface 22, such as patient name. The user interface 22 may be coupled to the transmit controller 32 to control the generation of ultrasound signals from the transducer array 26 and hence the images produced by the transducer array and the ultrasound system. The user interface 22 may also be coupled to the multiplanar reformatter 54 for selection and control of the planes of multiple multiplanar reformatted (MPR) images which may be used to perform quantified measures in the image field of the MPR images.

Again, it shall be noted that the aforementioned ultrasound system 100 has so far only been explained as one possible example for an application of medical 3D ultrasound image processing device 10. It shall be noted that the aforementioned ultrasound system 100 does not have to comprise all of the components explained before. On the other hand, the ultrasound system 100 may also comprise further components, if necessary. Still further, it shall be noted that a plurality of the aforementioned components do not necessarily have to be realized as hardware, but may also be realized as software components. A plurality of the aforementioned components may also be comprised in common entities or even in one single entity and do not all have to be realized as separate entities, as this is schematically shown in FIG. 2.

The ultrasound imaging system 100 according to the present invention further comprises a tracking unit 62 which is configured to determine a relative spatial position and orientation of each of the acquired plurality of 3D ultrasound image data with respect to each other. This tracking unit 62 may track the absolute spatial position and orientation of the plurality of 3D ultrasound image data. However, while tracking the absolute spatial position and orientation is not necessarily mandatory, it is at least required to track the relative spatial position and orientation of the 3D ultrasound image data with respect to each other. If the transducer controller 32 of the ultrasound acquisition unit 16 is arranged to steer the transmitted by the array ultrasound beams under different angles (thereby acquiring a plurality of 3D ultrasound image data having different partially overlapping field of views), the tracking unit 62 may be coupled directly to the transducer controller 32.

The two examples of an application of the present invention can be understood from FIG. 1. In the first example in order to acquire the 3D ultrasound image data having different partially overlapping field of views the ultrasound probe 14 is moved from a first position P1 to a second position P2. The tracking unit 62 determines the relative spatial position and orientation of a first 3D ultrasound image data corresponding to the first probe's position with respect to a second 3D ultrasound image data corresponding to the second probe's 14' position. This position and orientation tracking may be done either by means of an external tracking or by means of an image registration based approach. Generally, both, the external tracking and the image registration based approach, may also be combined with each other. In the second example the ultrasound acquisition unit 16 can be arranged to steer the transmitted ultrasound beams under different angles while the probe (14, 14') remains at the fixed position (either P1 or P2), in this case the tracking unit can determine the relative spatial position and orientation of the 3D image data based on the input from the transducer controller 32.

In case of an external tracking, the tracking unit 62 may e.g. comprise an electromagnetic tracking unit or an optical tracking unit comprising one or more cameras. These external tracking units preferably track the relative position and orientation of the ultrasound probe 14. Tracking the relative position and orientation of the ultrasound probe 14 enables determining the relative position and orientation of the acquired ultrasound volumes. This provides, for each voxel in the acquired imaging volume, a position in the 3D space.

Alternatively or additionally, an image registration based approach may be used for computing the relative positions and orientations of the acquired 3D ultrasound image data using rigid image registration approaches. The specific registration approach that is used is preferably selected depending on the tissue properties being scanned. In this scenario, the relative positions of the volume voxels are computed with respect to the previously acquired volume. The tracking unit 62 is thereto preferably configured to compare the plurality of acquired 3D ultrasound image data by means of an image analysis, and to perform the image registration based on said image analysis. The image registration is therefore based on an image comparison of the plurality of 3D ultrasound images, e.g. voxel by voxel.

Furthermore, the ultrasound imaging system 100 according to the present invention further comprises a stitching unit 64. The stitching unit 64 is configured to compound the plurality of 3D ultrasound image data, which have different but at least partially overlapping field of views, by stitching them to each other in order to generate compounded 3D ultrasound image data. The stitching unit 64 in other words combines a plurality of 3D ultrasound image data to a large area volume including the smaller volumes (field of views) represented in each of the plurality of separate 3D ultrasound image data. This enables a reconstruction of a 3D volume that is larger than the field of view of the ultrasound probe 14. This is specifically advantageous in the case of imaging a full organ that is larger than the field of view of the ultrasound probe 14. The 3D volume of the compounded image includes the several overlapping volumes of the different acquired 3D ultrasound image data. The final volume of the compounded 3D ultrasound image data are so to say based on a combination of the overlapping input volumes of the plurality of acquired 3D ultrasound image data.

The stitching unit 64 according to the present invention is configured to calculate a stitching order of the plurality of 3D ultrasound image data before stitching them together. This stitching order is calculated within the stitching unit 64 based on the determined relative spatial positions of the 3D ultrasound image data that have been determined before by means of the tracking unit 62. The calculation of said stitching order based on said determined relative spatial positions of the image data is used to minimize an overlapping area of the different field of views of the plurality of image data. Finally, the stitching unit 64 stitches the plurality of 3D ultrasound image data according to said stitching order. Minimizing the overlapping area of the different field of views of the plurality of 3D ultrasound image data by means of the calculated stitching order reduces the amount of stitches/seams between the compounded image data. This again increases the image quality of the finally compounded 3D ultrasound image data.

The herein proposed stitching method preferably defines a patch (p) stitching order that minimizes the overlapping area between consecutive patches (volume ($p(n) \not\subset p(n-1)$)). The overlapping area of the volumes of the different ultrasound data sets is correlated to the distance between the volumes of the different acquired 3D ultrasound data sets. The further away the volumes are from each other, the smaller the overlapping area is, until a given threshold, over which the overlapping area is zero. In addition, there is a dependency on the volume shape: The correlation is independent of the distance direction between the volumes of spherical shapes, however, for cone or rectangular based shapes, there is a dependency on the volume shape, which increases with the distance. It is herein assumed that for small distances, the correlation can be assumed to be quasi direction independent. Giving this assumption, the initial volume pre-alignment is performed using the center-of-mass point ($x\_i$) of each of the patches (p). This allows solving the sorting problem using a point cloud based approach.

To translate the above assumptions into a point cloud problem, the center of mass (x) of each patch ($p\_i$) are sorted where the distance path ($d\_i(x)$) for the volumes is maximized. Starting with the youngest volume center of mass ($x\_n$), the next furthest volume is selected, followed by the furthest away from the two patches and so forth. By selecting the voxel values in the final volume based on this ordering, it provides an approximation to the volume distribution which minimizes the presence of stitches in the final volume of the compounded 3D ultrasound image data.

Figure 3:
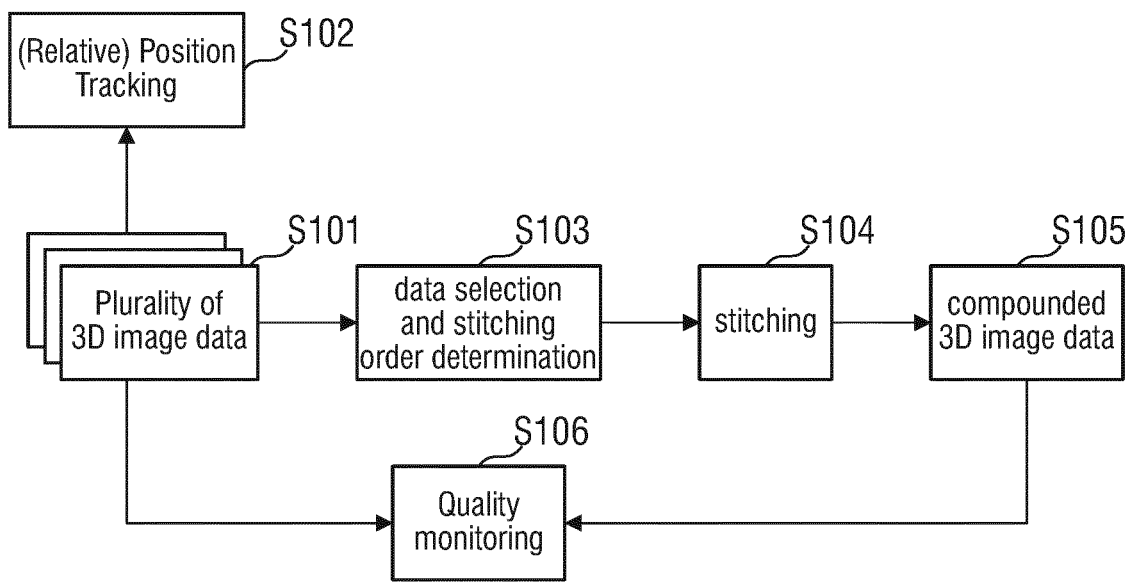
FIG. 3 shows a schematic block diagram illustrating principles of an embodiment of an ultrasound imaging method according to the present invention.

FIG. 3 summarizes the method according to the present invention in a schematical way. In a first step S101, a plurality of 3D ultrasound image data having different but at least partially overlapping field of views are acquired. In step S102, the relative spatial positions of each of the plurality of 3D ultrasound image data are determined with respect to each other or with respect to an absolute coordinate system. In step S103, the plurality of 3D image data are selected for the subsequent stitching in step S104. The data selection of step S103 includes a determination of the stitching order that defines which ultrasound image data are used for the subsequent stitching and in which order they are used one after the other. In contrast to state of the art techniques, the ultrasound image data are not stitched together in the order of their time and date they have been acquired, but in a stitching order that minimizes the overlapping area of the different field of views of the plurality of 3D ultrasound image data, so as to minimize the numbers of stitches/seams between the different images in the compounded 3D ultrasound image. The stitching order is determined in step S103 based on the relative positions determined in step S102. The stitching order is preferably calculated by determining distances between spatial positions of center points of each of the plurality of 3D ultrasound image data and ordering the plurality of 3D ultrasound image data according to said determined distances. The stitching in step S104 has preferably begun with one of the plurality of 3D ultrasound image data that has been acquired the latest in time and stitching it to one of the plurality of 3D ultrasound image data, the center point of which having the largest distance from the center point of the 3D ultrasound image data that has been acquired the latest in time. The stitching is then continued in step S104, preferably, by stitching a further one of the plurality of 3D ultrasound image data with the already stitched 3D ultrasound image data, wherein the center point of the further one of the plurality of 3D ultrasound image data has the largest distance (compared to the center points of all remaining not yet stitched ultrasound image data) from the center points of each of the already stitched 3D ultrasound image data.

By means of this stitching technique performed in step S104 using the stitching order determined in step S103, the compounded 3D ultrasound image data is finally computed in step S105.

Figure 5:
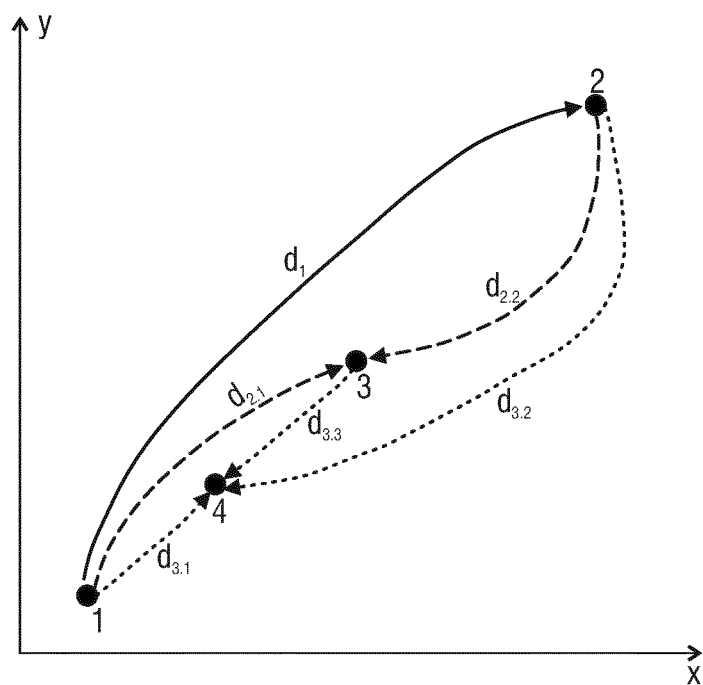
FIG. 5 shows a diagram schematically illustrating a determination of a stitching order according to an embodiment of the present invention.

The basic principle of determining the stitching order as explained above is visualized in schematical form for a simplified example in FIG. 5. Therein, four different ultrasound image data (indicated by points 1, 2, 3, and 4) are illustrated which all have different center points and therefore different field of views. The size of each field of view is assumed to be the same for all of the four 3D image data sets.

Image data set 1 is the youngest data set, i.e. the data set that has been acquired the latest. The stitching therefore begins with image data set 1 and stitches it to image data set 2, since the center point of image data set 2 has the largest distance $d_1$ from the center point of image data set 1 compared to the other data sets 3 and 4. Next, stitching is continued with image data set 3, since the distance of the center point of image data set 3 from the center points of image data sets 1 and 2 (i.e. the sum of $d_{2\_1}$ and $d_{2\_2}$) is larger than the distance of the center point of the remaining, not yet stitched image data set 4 from the center points of the data sets 1 and 2. Finally, data set 4 is stitched to the already stitched data sets 1, 2, and 3.

Figure 4:
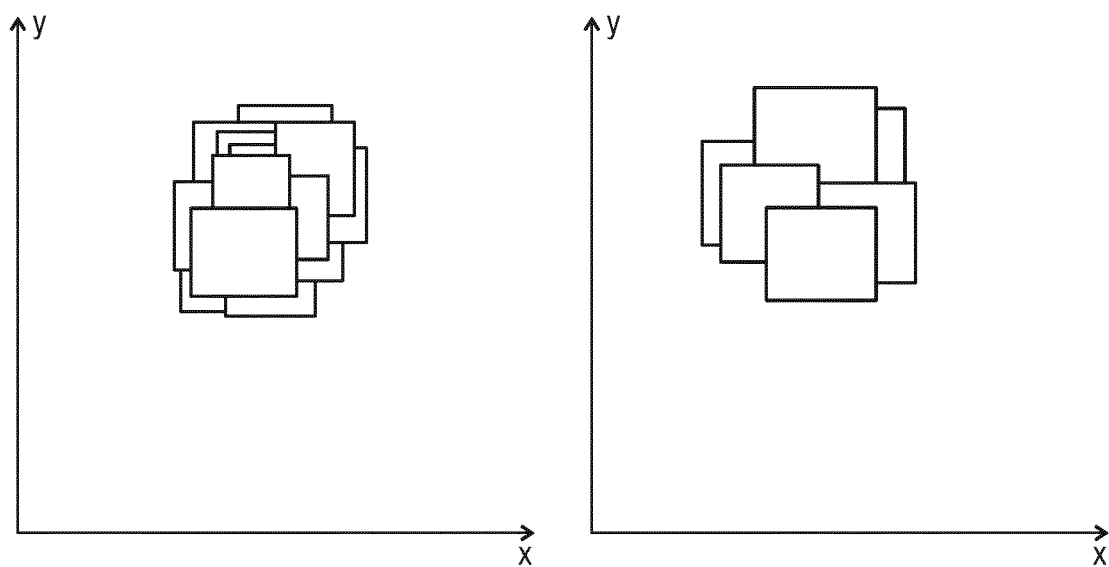
FIG. 4 shows a two schematic diagrams comparing an image compounding technique according to the prior art with the image compounding technique according to the present invention.

FIG. 4 schematically shows a comparison of a resulting compounded 3D image that results from a state of the art stitching technique using a stitching order according to the image data set age (see left side of FIG. 4) in comparison to a stitching order as defined according to the present invention which maximizes the patch contribution and minimizes the overlapping area of the different field of views of the plurality of 3D ultrasound image data (see right part of FIG. 4). It may be observed from this simplified, schematic example that the number of stitches/seams is significantly reduced with the stitching technique and its pre-performed stitching order determination according to the present invention.

As shown in FIGS. 2 and 3, the ultrasound imaging system 100 according to the present invention may furthermore comprise an image quality unit 66 and an alarm unit 68. These units 66, 68 may perform a quality monitoring as schematically shown in step S106 of FIG. 3. This quality monitoring mainly serves for monitoring anatomy changes and notifying the user of the system 100 if anatomy changes above a predetermined threshold occur within the acquired ultrasound image data. Thereto, the partial volume area acquired in real-time within each of the plurality of 3D ultrasound image data sets is compared to the compounded 3D image data. The metric used for computing said image difference may provide an absolute value providing an indication of the amount of image changes. The computed value can be used either as a real-time value specifying the image quality. This value may, for example, be shown to the user on the display 18. Alternatively, or additionally, the quality value determined in the image quality unit 66 may be provided to the alarm unit 68 which then informs the user that the currently acquired ultrasound image data are out-of-date, such that a new image acquisition is required. This alarm unit 68 may include a loudspeaker, an optical actuator, and/or a haptic actuator providing audible, visible, and/or haptic feedback to the user.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. Ultrasound imaging system configured to acquire a plurality of 3D ultrasound image data having different but at least partially overlapping field of views for producing a spatially compounded 3D ultrasound image data, comprising:
   at least one processor configured to determine a relative spatial position of each of the plurality of 3D ultrasound image data with respect to each other, and
   wherein the at least one processor is further configured to compound the plurality of 3D ultrasound image data, wherein the plurality of 3D ultrasound image data includes at least three 3D ultrasound image data, by stitching them to each other in order to generate a compounded 3D ultrasound image data,
   wherein the stitching includes determining a stitching order of the plurality of 3D ultrasound image data based on the determined relative spatial position of the 3D ultrasound image data for minimizing an overlapping area of the different field of views of the plurality of 3D ultrasound image data,
   wherein determining the stitching order includes determining distances between spatial positions of center points of each of the plurality of 3D ultrasound image data and ordering the plurality of 3D ultrasound image data based on the determined distances,
   wherein the stitching order begins with one of the plurality of 3D ultrasound image data that has been acquired comparatively the latest in time being stitched to another one of the plurality of 3D ultrasound image data, the center point of which having the comparatively largest distance from the center point of the one of the plurality of 3D ultrasound image data that has been acquired comparatively the latest in time,
   wherein the stitching order is further determined by selecting, as each subsequent 3D ultrasound image data to be stitched, the 3D ultrasound image data of remaining ones of the plurality of 3D ultrasound image data which is farthest from a preceding one of the 3D ultrasound image data,
   wherein the at least one processor is adapted to stitch the plurality of 3D ultrasound image data according to the stitching order,
   wherein the at least one processor is configured to continue stitching a further one of the plurality of 3D ultrasound image data with the already stitched 3D ultrasound image data,
   wherein the center point of the further one of the plurality of 3D ultrasound image data has the comparatively largest distance from the center points of each of the already stitched 3D ultrasound image data, and
   wherein the distance from the center points of each of the already stitched 3D ultrasound image data to the center point of the further one of the plurality of 3D ultrasound image data is computed as the sum of the distances from the center point of each of the already stitched 3D ultrasound image data to the center point of the further one of the plurality of 3D ultrasound image data.

2. Ultrasound imaging system as claimed in claim 1, wherein the center points of each of the plurality of 3D ultrasound image data are the center-of-mass points of respective 3D ultrasound image data volumes.

3. Ultrasound imaging system as claimed in claim 1, wherein the at least one processor is configured to determine the position of an ultrasound probe of the ultrasound imaging system by using an electromagnetic tracking unit.

4. Ultrasound imaging system as claimed in claim 1, wherein the at least one processor is configured to determine the position of an ultrasound probe of the ultrasound imaging system by using an optical tracking unit.

5. Ultrasound imaging system as claimed in claim 1, wherein the at least one processor is further configured to compare the plurality of 3D ultrasound image data by means of an image analysis, and to perform an image registration thereupon.

6. Ultrasound imaging system as claimed in claim 1, further comprising an image quality unit which is adapted to perform an image analysis of each newly acquired 3D ultrasound image data, and to calculate an image difference of the newly acquired 3D ultrasound image data and the compounded 3D ultrasound image data for determining an image quality factor of the newly acquired 3D ultrasound image data.

7. Ultrasound imaging system as claimed in claim 6, further comprising a display and a display control unit, wherein the display control unit is adapted to control the display to display the determined image quality factor.

8. Ultrasound imaging system as claimed in claim 6, further comprising an alarm unit which is adapted to generate an optical, audible and/or haptic alarm if the image quality factor falls below or exceeds a predetermined threshold value.

9. Ultrasound imaging method for producing spatially compounded 3D ultrasound image data, comprising the steps of:
  acquiring a plurality of 3D ultrasound image data having different but at least partially overlapping field of views, wherein the plurality of 3D ultrasound image data includes at least three 3D ultrasound image data;
  determining a relative spatial position of each of the plurality of 3D ultrasound image data with respect to each other;
  calculating a stitching order of the plurality of 3D ultrasound image data based on the determined relative spatial position of the 3D ultrasound image data for minimizing an overlapping area of the different field of views of the plurality of 3D ultrasound image data,
  wherein calculating the stitching order includes determining distances between spatial positions of center points of each of the plurality of 3D ultrasound image data and ordering the plurality of 3D ultrasound image data based on the determined distances,
  wherein the stitching order begins with one of the plurality of 3D ultrasound image data that has been acquired comparatively the latest in time being stitched to another one of the plurality of 3D ultrasound image data, the center point of which having the comparatively largest distance from the center point of the one of the plurality of 3D ultrasound image data that has been acquired comparatively the latest in time, and
  wherein the stitching order is further calculated by selecting, as each subsequent 3D ultrasound image data to be stitched, the 3D ultrasound image data of remaining ones of the plurality of 3D ultrasound image data which is farthest from a preceding one of the 3D ultrasound image data; and
  compounding the plurality of 3D ultrasound image data by stitching them according to the stitching order,
  wherein stitching is continued by stitching a further one of the plurality of 3D ultrasound image data with the already stitched 3D ultrasound image data,
  wherein the center point of the further one of the plurality of 3D ultrasound image data has the comparatively largest distance from the center points of each of the already stitched 3D ultrasound image data, and
  wherein the distance from the center points of each of the already stitched 3D ultrasound image data to the center point of the further one of the plurality of 3D ultrasound image data is computed as the sum of the distances from the center point of each of the already stitched 3D ultrasound image data to the center point of the further one of the plurality of 3D ultrasound image data.

10. Ultrasound imaging method as claimed in claim 9, wherein the center points of each of the plurality of 3D ultrasound image data are the center-of-mass points of a respective 3D ultrasound image data volume.

11. Non-transitory computer readable medium comprising instructions, which when executed by at least one processor of an ultrasound imaging system cause the ultrasound imaging system to:
  acquire a plurality of 3D ultrasound image data having different but at least partially overlapping field of views, wherein the plurality of 3D ultrasound image data includes at least three 3D ultrasound image data;
  determine a relative spatial position of each of the plurality of 3D ultrasound image data with respect to each other;
  calculate a stitching order of the plurality of 3D ultrasound image data based on the determined relative spatial position of the 3D ultrasound image data for minimizing an overlapping area of the different field of views of the plurality of 3D ultrasound image data,
  wherein calculating the stitching order includes determining distances between spatial positions of center points of each of the plurality of 3D ultrasound image data and ordering the plurality of 3D ultrasound image data based on the determined distances,
  wherein the stitching order begins with one of the plurality of 3D ultrasound image data that has been acquired comparatively the latest in time being stitched to another one of the plurality of 3D ultrasound image data, the center point of which having the comparatively largest distance from the center point of the one of the plurality of 3D ultrasound image data that has been acquired comparatively the latest in time, and
  wherein the stitching order is further calculated by selecting, as each subsequent 3D ultrasound image data to be stitched, the 3D ultrasound image data of remaining ones of the plurality of 3D ultrasound image data which is farthest from a preceding one of the 3D ultrasound image data; and
  compound the plurality of 3D ultrasound image data by stitching them according to the stitching order,
  wherein stitching is continued by stitching a further one of the plurality of 3D ultrasound image data with the already stitched 3D ultrasound image data,
  wherein the center point of the further one of the plurality of 3D ultrasound image data has the comparatively largest distance from the center points of each of the already stitched 3D ultrasound image data, and
  wherein the distance from the center points of each of the already stitched 3D ultrasound image data to the center point of the further one of the plurality of 3D ultrasound image data is computed as the sum of the distances from the center point of each of the already stitched 3D ultrasound image data to the center point of the further one of the plurality of 3D ultrasound image data.

* * * * *